(12) United States Patent
Kataoka et al.

(10) Patent No.: US 7,214,500 B2
(45) Date of Patent: *May 8, 2007

(54) BRUSH-LIKE STRUCTURED SURFACE OF POLY(ETHYLENE OXIDE) HAVING ELEVATED DENSITY

(75) Inventors: Kazunori Kataoka, Tokyo (JP); Yukio Nagasaki, Moriya (JP); Hidenori Otsuka, Kawasaki (JP); Katsumi Uchida, Kashiwa (JP); Tadahito Takahashi, Yokohama (JP); Miki Kato, Kashiwa (JP)

(73) Assignee: Toudai TLO, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/507,303

(22) PCT Filed: Mar. 7, 2003

(86) PCT No.: PCT/JP03/02744

§ 371 (c)(1),
(2), (4) Date: Oct. 7, 2004

(87) PCT Pub. No.: WO03/076933

PCT Pub. Date: Sep. 18, 2003

(65) Prior Publication Data

US 2005/0142028 A1 Jun. 30, 2005

(30) Foreign Application Priority Data

Mar. 11, 2002 (JP) ............................ 2002-065298

(51) Int. Cl.
  G01N 33/53 (2006.01)
  C12M 1/34 (2006.01)
  A61K 31/765 (2006.01)
  C07K 1/10 (2006.01)

(52) U.S. Cl. ................ 435/7.92; 435/287.2; 435/7.1; 530/402; 424/78.31

(58) Field of Classification Search ................ 436/525, 436/527; 525/535; 528/370, 373, 374; 435/7.92, 435/287.2, 7.1; 425/78.31; 530/402
See application file for complete search history.

(56) References Cited

U.S. PATENT DOCUMENTS

| 4,415,666 | A | 11/1983 | D'Orazio et al. |
| 5,204,239 | A * | 4/1993 | Gitler et al. ................. 435/7.1 |
| 5,242,828 | A | 9/1993 | Bergström et al. |
| 5,763,191 | A | 6/1998 | Knoll et al. |
| 5,925,720 | A | 7/1999 | Kataoka et al. |
| 5,929,177 | A | 7/1999 | Kataoka et al. |
| 5,973,069 | A | 10/1999 | Kataoka et al. |
| 6,235,340 | B1 * | 5/2001 | Lee et al. .................. 427/2.12 |
| 6,927,033 | B2 * | 8/2005 | Kataoka et al. ............. 435/7.1 |
| 2003/0171506 | A1 | 9/2003 | Kataoka et al. |
| 2004/0038506 | A1 * | 2/2004 | Kataoka et al. ............. 438/584 |

FOREIGN PATENT DOCUMENTS

| EP | 0 589 867 B1 | 4/1996 |
| EP | 1 279 959 A1 | 1/2003 |
| JP | 2815120 | 8/1998 |
| JP | 3071823 | 5/2000 |
| WO | 96/32434 | 10/1996 |
| WO | 96/33233 | 10/1996 |
| WO | WO 96/32434 | 10/1996 |
| WO | WO 96/33233 | 10/1996 |
| WO | 97/06202 | 2/1997 |
| WO | WO 97/06202 | 2/1997 |
| WO | 01/86301 A1 | 11/2001 |
| WO | WO 01/86301 | 11/2001 |

OTHER PUBLICATIONS

Ostuni et al. The interaction of proteins and cells with self-assembled monolayers of alkanethiolates on gold and silver. 1999 Colloids and Surfaces B: Biointerfaces, vol. 15, pp. 3-30.*

Otsuka et al. Quantitative and reversible lectin-induced association of gold nanoparticles modified with alpha-lactosyl-w-mercapto-poly(ethylene glycol). 2001 J. Am. Chem. Soc, vol. 123, pp. 8226-8230.*

Szabo, A. et al., "Surface plasmon resonance and its use in biomolecular interaction analysis (BIA)", *Current Opinion in Structural Biology*, vol. 5, pp. 699 to 705 (1995).

Roberts, C. et al., "Using Mixed Self-Assembled Monolayers Presenting RGD and (EG)$_3$OH Groups To Characterize Long-Term Attachment of Bovine Capillary Endothelial Cells to Surfaces", *J. Am. Chem. Soc.*, vol. 120, pp. 6548 to 6555 (1998).

Holmlin, R. E. et al., "Zwitterionic SAMs that Resist Nonspecific Adsorption of Protein from Aqueous Buffer", *Langmuir*, vol. 17, pp. 2841 to 2850 (2001).

Pavey, K. et al., "SPR analysis of the total reduction of protein adsorption to surfaces coated with mixtures of long- and short-chain polyethylene oxide block copolymers", *Biomaterials*, vol. 20, pp. 885 to 890 (1999).

Lu, H. B., "Attachment of Functionalized Poly(ethylene glycol) Films to Gold Surfaces", *Langmuir*, vol. 16, pp. 1711 to 1718 (2000).

* cited by examiner

*Primary Examiner*—Long V. Le
*Assistant Examiner*—Shafiqul Haq
(74) *Attorney, Agent, or Firm*—Wenderoth, Lind & Ponack, L.L.P.

(57) ABSTRACT

A surface on which adsorption of protein (e.g., BSA) is markedly suppressed is provided, by contacting solutions of polymers whose chief component is poly(ethylene oxide) having binding sites to sensor surfaces with biosensor surfaces plural times to link the polymers.

2 Claims, 5 Drawing Sheets

BRUSH-LIKE STRUCTURED SURFACE OF POLY(ETHYLENE OXIDE) HAVING ELEVATED DENSITY

RELATED APPLICATIONS

This is a US national phase filing under 35 U.S.C. § 371 of PCT/JP03/02744 filed Mar. 07, 2003 and claims priority from JP 2002-65298 filed Mar. 11, 2002.

Japanese Patent No. 3071823 (corres. to U.S. Pat. No. 5,763,191 and EP 0 574 000B1) describes a surface formed of a spacer molecule ($C_1$–$C_{30}$ alkylene chain) which links onto a support member via a sulfur atom (of mercapto group) and to which covalently bonded are, by order, a hydrophilic linker (a straight chain molecule of 4 to 15 atoms in chain length) and a solid phase reactant (biotin derivative residue). The same patent also describes a compound expressed by the following formula, as a typical biotinylated compound which forms such a surface:

TECHNICAL FIELD

This invention belongs to the art of biosensors. More specifically, the invention relates to a biosensor surface which reduces or prevents non-specific adsorption or linkage thereonto of impurities other than intended analyte, which are contained in biological fluids or the like.

BACKGROUND ART

For detection of analytes present in biological samples, biosensors having a large variety of detection systems have been proposed. Of known biosensors, those utilizing surface plasmon resonance (SPR) are sensitive to changes in refractive index at surfaces and in the vicinities thereof of thin metal films (e.g., see A. Szabo, et al., *Curr. Opin. Strnct. Biol.* 5(1995) 699–705). SPR enables an in situ observation of procedures occurring between a surface and complex biological solutions that allows, e.g., acquisition of data from analytes in real time without requiring tagging of the analytes. It, therefore, is suitable for obtaining both kinetic and thermodynamic parameters, and hence SPR sensor is one of those biosensors which are drawing attention.

As a typical biosensor chip having this kind of surface, BIACORE® which is commercially available from Amersham Pharamacia Biotech., Inc. can be named, which is provided in form of a chip in which a translucent matrix of dextran with carboxylated ends is immobilized on a thin gold film. A patent which is considered to claim such a detection surface is Japanese Patent No. 2815120 (corresponding to U.S. Pat. No. 5,242,828 and EP 0 589 867B1) Gazette. This Official Gazette describes a surface formed by the steps of linking organic molecules expressed by a formula HS—R—Y (wherein R stands for a hydrocarbon chain having a chain length exceeding ten atoms and which may be interrupted with hetero atom(s), and Y stands for a ligand or an active group for covalently bonding a biocompatible porous matrix thereto) onto a membrane surface of the free-electron metal such as gold, silver or the like via the thiol (or mercapto) groups therein, whereby covering said surface with a close-packed monolayer of said organic molecules, and thereafter covalently bonding to the surface a hydrogel as said biocompatible porous matrix, said hydrogel comprising agarose, dextran, polyethylene glycol and the like which may have functional group(s) for linking the ligand.

The molecular chains on said surface which have solid phase reactant may further be diluted with diluting molecules which do not have the solid phase reactant (i.e. in the above formula for example, biotin derivative residue), or which have neither the solid phase reactant nor hydrophilic linker.

Roberts et al., *J. Am. Chem. Soc.*, 1998, 120, 6548–6555 describes formation of self-assembled mono-molecular layer (SAM) on a golden surface via mercapto groups, using a compound based on HS-spacer molecule ($C_{11}$ alkylene chain)-hydrophilic linker (a chain formed of 3 or 6 ethylene oxide units). This document also teaches that a surface formed of a mixture of a compound whose hydrophilic linker portion consists of 3 ethylene oxide units and a compound whose hydrophilic linker portion consists of 6 ethylene oxide units (an oligopeptide ligand binding to its end) promotes cells' ligand-specific binding but reduces accumulation of proteins by so bound cells. Holmlin et al., *Langmuir.* 17, 2841–2850 (2001) also discusses suppression of protein adsorption onto a surface containing said SAM and ampholytic ion.

Pavey et al., *Biomaterials,* 20 (1999) 885–890 discloses a surface onto whose SPR detecting thin metal film various combinations of two kinds of poly(ethylene oxide)$_n$-poly(propylene oxide)$_m$-poly(ethylene oxide)$_n$ triblock copolymers are adhered, with a suggestion that on so formed surfaces poly(ethylene oxide) chains would extend in the solution to form a brush-like architecture. Furthermore, the document shows: on the surfaces onto which two kinds of triblock copolymers of different poly-(ethylene oxide) chain length (n) are adhered, generally protein (bovine serum albumin) adsorption is less, compared with the surfaces to which one kind only of said triblock copolymer is adhered.

Among the foregoing prior art documents, Japanese Patent No. 2815120 discloses that a monolayer surface in which organic molecules are densely packed can be obtained by chemical adsorption of an organic compound whose chain (R) length exceeds 10 atoms, preferably 12–30 atoms, e.g., 16-mercaptohexadecanol having hydrophobic, considerably large alkylene chain, onto a metal surface via thiol group. So obtained monolayer exhibits storage stability, and the patent furthermore suggests it also can be an effective barrier layer to protect the metal surface from chemical corrosion. Onto such a barrier layer a hydrogel which minimizes protein compatibility and non-specific interaction is bound. Hence aforesaid BIACORE® (carrying hydrogel of dextran) which likely is a preferred embodiment of said patented invention has been reduced to practice. It is, however, by no means easy to have the barrier layer uniformly carry the hydrogel and precise operations are required. Also although non-specific adsorption of protein is considerably reduced, there is still room for further improvement.

Where biotinyl (solid phase reactant) on the surface formed of aforesaid biotinylated compound is densely present, said Japanese Patent 3071823 dared to sparsely bind the biotinylated compound onto the surface of a support material, or link to the surface both said diluent molecules and molecules having biotynyl residue (solid phase reactant), by using the diluent molecules having no biotynyl residue and the corresponding molecules having biotynyl residue at a ratio of 10:1–2:1, for improving slow binding of, for example, biotin and free avidin which forms non-covalently bonded pair with biotin. Such a surface or that proposed by Roberts et al. have hydrophilic linker portion formed of up to about 5 to 6 ethylene oxide units but do not have a hydrogel layer like the one in Japanese Patent 2815120, and hence may cause non-specific adsorption of impurity proteins other than the object protein (e.g., streptavidin) or cells.

Pavey et al. adheres said triblock copolymers onto a metal surface via their hydrophobic blocks, i.e., poly(propylene oxide) domain, and it is difficult to obtain a surface with stability, uniformity and reproducibility, like ordinary polymer coating (cf. U.S. Pat. No. 4,415,666). Moreover, it is also difficult to raise density of poly-(ethylene oxide) chains.

A part of the present inventors discovered, as a surface from which such shortcomings of those prior art surfaces as above described were removed or reduced, a surface prepared by the steps of dissolving a polymer formed mainly of poly(ethylene oxide) (which may hereafter be abbreviated as PEG) having mercapto (—SH) group at one end and the other end being optionally protected, in a buffer solution, and contacting said solution with golden surface of an SPR sensor chip for about an hour. They found that non-specific protein adsorption onto said surface could be reduced at least to the level equivalent to that onto the commercial BIACORE® sensor chip surface CM5, and have filed a patent application directed to such a surface (cf. WO 01/86301).

According to said Japanese Patent 2815120, the R in said HS—R—Y chains must be a hydrocarbon group having at least 10 atoms, to enable to closely pack the metal surface with said chains. Whereas, according to the Japanese Patent 3071823, a biotinylated compound having a hydrophilic linker of a chain length, for example, of 4–15 atoms (1–3 of ethylene oxide units) is used to forms a surface on which chains of said compound are sparsely linked. Surprisingly, however, according to said WO 01/86301, the inventors thereof discovered macromolecules which are entirely different form those polymers described in U.S. Pat. No. 3,071,823 or Roberts et al. in that the former comprises such long chain polymers as that their PEG domain has a molecular weight of 1,000–10,000, could be effectively linked to the metallic surface via their mercapto groups, in an aqueous solution. That is, when such a polymer as described in WO 01/86301 is used, the hydrophilic PEO chains and proteins in the solution cause spatial repulsion, and it was a common recognition among skilled artisans that a PEO layer which was hydrated to reduce such an interaction at the surfaces was flexible and mobile. Nevertheless, the desired amount (or at an adequate density) of said PEO chains are found to be stably linked to the surface.

Whereas, for the surface as described in WO 01/86301, further reduction in non-specific adsorption of impurity proteins thereon is desirable if all possible, similarly for BIACORE® sensor surface. Therefore, the present invention aims at provision of a surface which enables further reduction in non-specific adsorption thereonto, compared with the surface described in WO 01/86301.

DISCLOSURE OF THE INVENTION

Although not intended to theoretically bind the invention, probably because PEO chains in a solution are mobile and sterically repulse each other as stated above, it is impossible to significantly increase the linked amount of the polymer by the liking method as described in WO 01/86301, even when the treating time is extended. We discovered, however, when the linking operations are repeated anew, additional polymer could be newly linked to the same surface at a higher density. Furthermore, it has been confirmed that adsoroption of impurity protein [e.g., bovine serum albumin (BSA)] to so obtained surface could be significantly reduced from that to the surface described in WO 01/86301.

Accordingly, therefore, the present invention provides a surface which is characterized in that (a) it is a biosensor surface to which at least one of the polymers expressed by a general formula, $$A\text{-}(CH_2)_p\text{-}L_1\text{-}(CH_2CH_2O)_n\text{-}L_2\text{-}X \qquad (I)$$

[in which
A stands for HS— or group,
where $R^1$, $R^2$ and $R^3$ each independently stands for $C_1$–$C_6$ alkyl,
$L_1$ stands for a first linker or valence bond,
$L_2$ stands for a second linker or valence bond,
X stands for hydrogen, a functional group, protected functional group or ligand,
p is an integer of 2–12,
n is an integer of, on the average, at least 10, preferably 20–10,000]

is linked via the A-moiety thereof, and that (b) the number of the polymer chain per 1 nm² of said surface is at least 0.1 (preferably at least 0.25) as converted from the data obtained by thermogravimetric analysis of said surface.

The present invention furthermore provides a method for preparing an embodiment of above-described surface, which comprises (A) a step of contacting an aqueous solution of a polymer expressed by a general formula (Ia), $$HS\text{---}(CH_2)_p\text{-}L_1\text{-}(CH_2CH_2O)_n\text{-}L_2\text{-}X \qquad (Ia)$$

(in which $L_1$, $L_2$, X, p and n have the same significations to those as defined as to the foregoing general formula (I))

with a surface of a metal selected from the group consisting of gold, silver, copper and aluminum, under the conditions sufficient to link a prescribed amount of said polymer to said metallic surface, and thereafter washing away the unlinked polymer, (B) a step of subsequently contacting an aqueous solution of a polymer which may be same or different from the polymer linked to the metallic surface in the above step and which has a small average value of the integer n (i.e., number of ethylene oxide units) with the metallic surface which has undergone the above step (A), under the conditions sufficient to link said polymer to said surface, and thereafter washing away the unlinked polymer; and (C) repeating a step similar to the above step (B) with so obtained surface plural times (generally 2–6 times, preferably 3–4 times).

As still another embodiment of the invention, there is provided a method for preparing a surface as above-described, in which A moiety in the general formula (I) is trialkoxysilyl group, which comprises (A) a step of contacting an organic solvent solution of a polymer expressed by a general formula (Ib), (in which $R^1$, $R^2$, $R^3$, $L_1$, $L_2$, X, p and n have the same significations to those as defined as to the general formula (I))

with a material selected from the group consisting of glass, semi-conductors, ceramics, metal oxides and alloy oxides, under the conditions sufficient to adhere or link a prescribed amount of said polymer to the surface of said material, distilling the solvent off, and washing away the unlinked polymer;

(B) a step of subsequently contacting an organic solvent solution of a polymer which is same or different from the polymer linked to the material surface in the above step and which has a small average value of the integer n (i.e., number of ethylene oxide units) with the surface which has undergone the above step (A) under the conditions sufficient to adhere or link said polymer to said surface, then distilling the solvent off and washing away the unlinked polymer; and (C) repeating a step similar to above step (B) with so obtained surface plural times.

As still another embodiment, the invention provides a method of preparing a surface as above-described, in which a mixture of at least two polymers of the general formula (Ia) or (Ib) whose n values differing form that of the first polymer by at least 10, preferably at least 20, is used.

BEAT EMBODIMENT FOR PRACTICING THE INVENTION

The parameter, $\Delta\theta[°]$, which indicates the degree of BSA adsorption onto such surfaces following the present invention, is a value induced by change in refractive index at metallic surface, as described in, e.g., Jung et al., *Langmuir*, 1998, 14, 5636, larger values indicating greater amount of BSA adsorption. This value is variable depending on individual measuring conditions, and in this invention $\Delta\theta[°]$ values are those measured following later-described "nonspecific adsorption test".

"Presuming each polymer to correspond to one expressed by the general formula (I) in which A is HS—, and -$L_2$-X is —$CH_2CH_2CH(OCH_2CH_3)_2$" said in this specification signifies: properties of polymer of the general formula (I) whose A is other than HS—, and -$L_2$-X is other than —$CH_2CH_2CH(OCH_2CH_3)_3$, were presumed, hypothesizing that their A is HS and -$L_2$-X is —$CH_2CH_2CH(OCH_2CH_3)_2$.

In the definition of n in the general formula (I), "n as an average value" or "n is an integer of, on the average" signify that the polymers represented by said general formula (I) normally have a certain fixed range of molecular weight distribution. According to later given production examples of the polymers, substantially mono-dispersible polymers were obtained, but not limited to such polymers, polydispersible polymers (e.g., whose weight-average molecular weight ($\overline{M}_w$) to number-average molecular weight ($\overline{M}_n$) ratio, $\overline{M}_w/\overline{M}_n$, is 1.6–2.0) can also be used in this invention, provided they satisfy said definition.

While biosensor surfaces utilizing SPR are mainly conceived as the surfaces following the present invention, the invention encompasses any other biosensor surfaces allowing tracing of certain changes occurring at the surfaces due to formation of a biologically specific non-covalent bond between wide varieties of ligand and receptor, e.g., antigen or hapten and antibody, sugar and lectin, substrate and enzyme, hormone and receptor thereof, oligonucleotide and complementary chain thereof and the like. As the traceable signals, they may be changes in radioactivity, contact angle, sedimentation, UV spectrum, surface plasmon resonance or the like.

Most of the polymers useful for the surfaces of the present invention are known per se. The polymers in which A represents HS— are described in said WO 01/86301, which are expressed by the general formula (Ia),

(in which $L_1$, $L_2$, X, p and n have the significations as previously defined). Depending on the production method, the optimum groups can be selected as $L_1$, $L_2$, and X, respectively. $L_1$ and $L_2$ may be a valence bond or various kinds of linker independently of each other. As specific examples of $L_1$ linker, the typical are —COO— (which group binds to an ethylene oxide unit via the oxygen atom), —O— and —S—. Specific examples of $L_2$ linker are —$(CH_2)_q$— (where q is an integer of 2–6).

X stands for hydrogen, a functional group or a protected functional group, which functional group may be any which is capable of covalently bonding with said ligand. Taking a case, for example, wherein the ligand is a protein or nucleotide, the functional group or protected functional group may be wherein $R^b$ each independently stands for hydrogen or $C_1$–$C_6$ alkyl, $R^c$ each independently stands for $C_1$–$C_6$ alkyloxy (ketal or acetal), or the two $R^c$s may together stand for an oxy (in which case the group as a whole becomes an aldehyde or formyl group: —CHO), or $R^c$ may be an optionally $C_1$–$C_6$ alkyl-substituted 1,2-dioxyethylene (forming a cyclic ketal). In particular, aldehyde (or formyl) group or protected aldehyde (or formyl) group (ketal group) can be conveniently used. $C_1$–$C_6$ alkyl specifically are methyl, ethyl, n-propyl, iso-propyl, n-butyl, sec-butyl, n-hexyl and the like, methyl being preferred. Typical preparation processes which are described in said WO 01/86301 are illustrated by the following reaction schemes.

Again, most of the polymers expressed by the general formula (Ib) in which A is trialkoxysilyl group:

(in the formula, $R^1$, $R^2$, $R^3$, $L_1$, $L_2$, X, p and n are same as previously defined) are known per se.

Reaction scheme 1:

(in the above formulae, Xa stands for X-$L_2$, and other symbols have the same significations as previously defined).

As another embodiment, polymers of said general formula (Ia) can be prepared according to the following reaction scheme 2, the method being more specifically described later.

Reaction scheme 2:

More specifically, $C_1$–$C_6$ alkyl in the definition of $R^1$, $R^2$, and $R^3$ have the same signification to those in the definition of $R^b$ and $R^c$. Also in the general formula (Ib), -X may have the same signification to that of X in the general formula (Ia); $L_1$ is, for example, —O—, —NHCOO— (binding to an ethylene oxide unit via the oxygen atom) or —N($R^d$)—($R^d$ being $C_1$–$C_6$ alkyl); and $L_2$ is —($CH_2$)$_\gamma$— or $CO(CH_2)_\gamma$— ($\gamma$ being an integer of 2–6). Such polymers can be conveniently prepared according to, e.g., any of the following reaction schemes.

Reaction scheme 3:

Reaction scheme 4:

Reaction scheme 5:

(in the above formula, M stands for potassium, sodium or lithium).

The foregoing living polymerization steps can be carried out under those reaction conditions known per se (e.g., see WO96/32434, WO97/06202, etc.). Otherwise, they can be carried out following the working Examples given later, or by modifying the conditions described therein.

While not in any limitative sense, in forming the surfaces using above described polymer(s) of the general formula (Ia), the support surfaces (thin metallic membrane on SPR sensor) is preferably selected from such metals as gold, silver, copper, aluminum and the like. Whereas, when the polymer(s) of the general formula (Ib) are used, it is convenient to select the support from glass, semi-conductor, ceramic, metal oxide and alloy oxide, which form hydroxyl groups on the surface with moisture or the like, said hydroxyl groups forming covalent bonds with trialkoxysilane.

The surfaces following the present invention which are either subjected to plural times' polymer-linking treatments using solutions containing polymers of the general formula (Ia) or (Ib), or to a linking treatment using a solution containing at least two polymers differing in their ethylene oxide unit (average value) number, have significantly increased amount of linked polymer(s) compared to that resulting from such a treatment given single time, notwithstanding the fact that said single linking treatment with substantially identical polymer(s) brings about fixed, approximately-saturated linkage group. Where a polymer of the general formula (Ia) is used, the polymer is dissolved in a suitably buffered aqueous solution, and the solution is contacted with the support surface at an adequate temperature, e.g., ambient temperature, (20–37° C.). Depending on the molecular weight of the polymer used, the optimum polymer concentration in the solution varies, while normally a concentration of 0.1–5 mg/ml, preferably 1 mg/ml is selected. The contact is carried out by contacting such a polymer solution with the support surface and incubating for several tens minutes to several hours.

Thus a fixed amount of the polymer is linked (presumably by chemical bonding) to the support surface. Unlinked polymer is removed from the surface by washing. Any washing liquid can be used so long as it can effectively remove the unlinked polymer, while use of diluted NaOH aqueous solution is preferred. After completion of the washing, the surface is subjected to another polymer-linking treatment using a polymer solution anew. This second linking treatment may be substantially identical with the first linking treatment including the washing. Preferably, the second linking treatment and washing are repeated at least one more time. The polymer used in the second and subsequent linking treatments may be the same to that used in the first treatment, or may have in each time a different poly (ethylene oxide) block molecular weight from that of the polymer used in the first treatment. Where their molecular weights are different, preferably the molecular weight of the polymer used in the second treatment is less than that of the first used polymer. The molecular weight of the polymer may be gradually reduced as the linking treatment is repeated. Although not in limitative sense, preferred combination of polymers used in the first linking treatment and the second and subsequent linking treatments, based on the molecular weight of the poly(ethylene oxide) block, comprises using a polymer of the general formula (I) or (Ia) having an integer n, as an average value, of 50–10,000 in the first linking treatment, and using a polymer having an ethylene oxide unit number less than that of the first used polymer by at least 10, preferably at least 50. Whereby a surface carrying at least $0.1/nm^2$ of the polymer chain, as converted from data obtained by thermogravimetric analysis of the same surface (cf. for example, W. P. Wuelfing et al., *J. Am. Chem. Soc.*, 1998, 120, 12696–12697) is conveniently obtained.

Where the polymer of the general formula (Ia) is replaced with a polymer of the general formula (Ib), the polymer is dissolved preferably in an anhydrous organic solvent. (for example, an easily polymer-soluble organic solvent such as toluene) and the solution is used for a linking or adhering treatment of the polymer to a surface of, for example, glass, titanium, aluminum or the like (if necessary after a hydroxylating treatment), the solvent is distilled off, and the polymer which unreacted with the surface is washed away with the same organic solvent to form the intended surface, all other features being the same to those in the case of using a polymer of the general formula (Ia).

On thus formed surface a high molecular brush-like architecture of polyethylene glycol [or poly(ethylene oxide)] of a higher density is formed, as compared with the surface obtained by a similar single polymer-linking treatment, whereby markedly reducing adsorption of impurity proteins in a sample which induce non-specific adsorption onto biosensor surfaces. Furthermore, the surfaces according to the present invention enable more precise detection of specific interactions between biological molecules. Hereinafter the present invention is explained in further details, referring to specific examples which are not intended to limit the present invention in any way.

POLYMER PRODUCTION EXAMPLE 1

Synthesis of acetal-PEG-SH (Mn=2000, 5000) (cf. Reaction Scheme 1)

Distilled tetrahydrofuran (THF) 20 ml and 3,3-diethoxy-1-propanol, an initiator, 0.2 mmol (0.032 ml) were added to an argon-substituted reactor, and further an equivalent amount of potassium naphthalene was added, followed by 15 minutes' stirring to conduct metallization. Then ethylene oxide 22.7 mmols (1,135 ml) was added, followed by two days' stirring at room temperature to conduct the polymerization. As a reaction-suspending agent, N-succinimidyl-3-(2-pyridylthio)propionate (SPDP) 0.4 mmol (0.125 g) was dissolved in a small amount of distilled THF and into the resultant solution said polymerization reaction solution was dropped under cooling with ice, through an isopiestic dropping funnel. After an overnight's stirring, the reaction was suspended and the polymer was recovered by the series of operations as washing with saturated saline solution, extraction with chloroform, reprecipitation from ether and lyophilization with benzene. The construction of the recovered polymer was confirmed with $^1$H-NMR, and the amount of SPDP residue introduced into the polymer terminals was confirmed by UV absorption of 2-thiopyridone which was released upon reaction with 2-mercaptoethanol.

PEG-SS-Py $2.0 \times 10^{-2}$ mmol (100 mg) was dissolved in 4 ml of distilled water, to which further 5 molar times thereof of dithiothreitol 0.1 mmol (15.42 mg) was added, followed by 30 minutes' stirring at room temperature. After the reaction, a polymer whose PEG segment had a Mn=5000 (hereafter abbreviated as PEG 5000) was recovered through a series of operations as washing with saturated saline solution, extraction with chloroform and reprecipitation from ether. The construction of the recovered polymer was confirmed with $^1$H-NMR and the amount of the terminal SH groups was determined by the reaction with 2-pyridyldisulfide (2-PDS).

Furthermore, substantially the same operations as above were repeated except that the feed amount of said ethylene oxide was decreased to produce a polymer with a PEG segment having a Mn=2000, "Mn" herein means the molecular weight of the PEG segment.

POLYMER PRODUCTION EXAMPLE 2

Synthesis of acetal-PEG-SH (Mn=2000, 5000) (cf. Reaction Scheme 2)

Under argon-substitution, into a flask 60 ml of THF as a solvent was fed at room temperature, and into which 1 mmol of 3,3-diethoxy-1-propanol as an initiator and 1 mmol (0.316 mol/liter) of K-naphthalene were added under stirring to effect metallization. After thorough stirring, 112.99 mmols of ethylene oxide was added, followed by 2 days' stirring under cooling with water to carry out the polymerization.

After the 2 days' stirring, 0.5 mmol of K-naphthalene and 4.5 mmols of triethylamine were added to the solution for the purpose of remetallization. In an eggplant type flask under argon-substitution, 3.5 mmols of methyl-sulfonyl chloride as an initiator was dissolved in 10 ml of THF solvent, and into the solution the above PEG polymer solution was added dropwise through an isopiestic dropping funnel. After the end of the dropping, the polymer was recovered by reprecipitation from diethyl ether, extracted with chloroform and saturated slaine solution, dehydrated over anhydrous $Na_2SO_4$ and recovered by lyophilization with benzene.

To 0.44 mmol of vacuum-dried sodium o-ethyldithiocabonate, 50 ml of THF and 3.6 ml of dimethylformamide (DMF) as the solvent were added in argon atmosphere, and this solution was added to 0.2 g of vacuum-dried acetal-PEG-MS, followed by 4 hours' reaction at room temperature. Thereafter the polymer was extracted with chloroform and saturated saline solution, dehydrated over anhydrous $Na_2SO_4$, purified by reprecipitation from diethyl ether and recovered by lyophilization with benzene. Further to 0.1 g of the vacuum-dried acetal-PEG-dithiocarbonate, 10 ml of THF was added as the solvent in argon atmosphere, and into which n-propylamine was added to form a 1.4M THF solution, followed by 3 hours' stirring to carry out the reaction. After the reaction the polymer was extracted with chloroform and saturated saline solution, dehydrated over anhydrous $Na_2SO_4$, purified by reprecipitation from diethyl ether, and a polymer with PEG segment having a Mn=5000 ("PEG 5000") was recovered by lyophilization with benzene. A structural analysis by $^1$H-NMR and GPC measurement of the recovered polymer were conducted, to confirm acquisition of above acetal-PEG-SH. Furthermore, substantially the same operations as above were repeated except that the feed amount of said ethylene oxide was decreased, to produce a polymer with a PEG segment having a Mn=2,000. This polymer is hereafter abbreviated as PEG 2000. "Mn" herein means the molecular weight of the PEG segment.

EXAMPLES 1–8

Immobilization of PEG onto JI Sensor Chips

A solution each of the polymers obtained in the above Production Examples at a concentration of 1.0 mg/ml [solvent: 1M NaCl-containing 50 mM phosphate buffer (pH7.3)] was let flow over the golden surface of JI sensor chip (procured from BIACORE) at 37° C., for 20 minutes at a flow rate of 20 µl/min. Then the surfaces were washed twice with a 50 mM NaOH solution for 30 seconds each, at a flow rate of 20 µl/min. This series of operations constituting one cycle of the immobilization experiment, surfaces on which those polymers were immobilized were prepared by the following procedures.

Example 1 (Control)

PEG 5000 (1) . . . one cycle immobilization of PEG 5000 on the golden surface, parenthesized numeral indicating the cycle number of immobilization experiment Example 2 (Control)

PEG 2000 (1) . . . one cycle immobilization of PEG 2000 on the golden surface

Example 3 (Present Invention)

PEG 5000 (1)+PEG 2000 (1) . . .
one cycle immobilization of PEG 5000 on the golden surface, followed by one cycle immobilization of PEG 2000 on the same golden surface Example 4 (Present Invention)

PEG 5000 (1)+PEG 2000 (3) . . .
one cycle immobilization of PEG 5000 on the golden surface, followed by three cycles of PEG 2000 immobilization on the same golden surface Example 5 (Present Invention)

PEG 5000 (1)+PEG 2000 (5) . . .
one cycle immobilization of PEG 5000 on the golden surface, followed by 5 cycles of PEG 2000 immobilization on the same golden surface Example 6 (Present Invention)

PEG 5000 and PEG 2000 (1) . . .
one cycle immobilization of a PEG 5000 and EG 2000 mixture on the golden surface, using a solution of said mixture Example 7 (Present Invention)

PEG 5000 (4) . . . four cycles of PEG 5000 immobilization on the
golden surface

Example 8 (Present Invention)

PEG 5000 (4)+PEG 2000 (3) . . .
four cycles of PEG 5000 immobilization on the golden surface, followed by 3 cycles of PEG 2000 on the same golden surface Non-specific Adsorption Test (1)

Over each of the surfaces of those JI sensor chips as obtained in Examples 1–8, untreated CM5 (formed by adsorbing carboxymethyldextran (acquired from BAIACORE onto a JI sensor chip) and blocked CM5 (formed by blocking the above carboxymethyl groups), bovine serum albumin (BSA) solution at a concentration of 1 mg/ml [solvent: 0.15 M NaCl-containing 10 mM HEPES buffer solution (pH 7.4)+3 mM EDTA and 0.005% (v/v) surfactant P20] was let flow at 25° C. for 10 minutes at a flow rate of 20 µl/min.

Three (3) minutes after the end of injection of said BSA solution, BSA linked to each of the surfaces was quantified. Untreated CM5 was used in the state as purchased from the market. Whereas, blocked CM5 was prepared by the steps of ① a NHS/EDC mixed solution was let flow over the untreated CM5 surface at a flow rate of 10 µl/min. for 10 minutes, ② then an ethanolamine solution was let flow over the same surface at a flow rate of 10 µl/min. for 10 minutes, and finally 50 mM NaOH solution was let flow at a flow rate of 10 µl/min. for 1 minute. This last washing was conducted three times to block the carboxymethyl groups. The results were as shown in FIG. 1.

Figure 1:
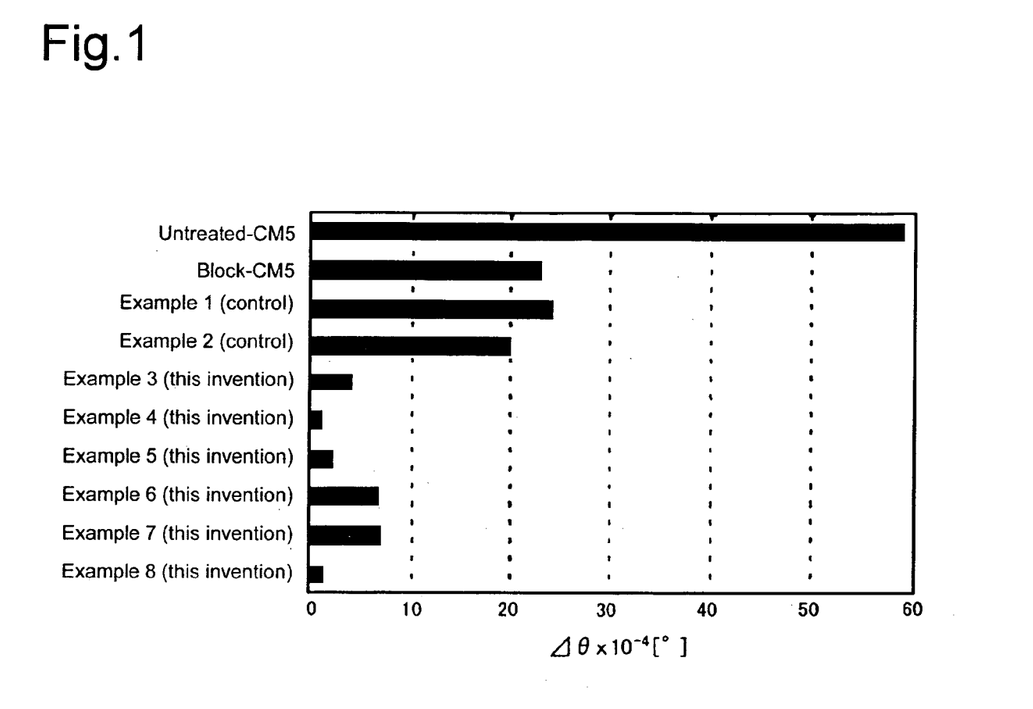
FIG. 1 is a graph showing the results of BSA adsorption test given to surfaces including those following prior art.

From FIG. 1, it can be understood that BSA adsorption onto the surfaces following the present invention was markedly less compared with commercialized untreated CM5 and blocked CM5, and furthermore with Example 1 (control) and Example 2 (control).

Non-specific Adsorption Test (2)

(Evaluation as for Proteins other than BSA)

This test was conducted for the purpose of comparing the amount of non-specifically adsorbed protein on a surface onto which PEG 5000 alone was immobilized, with that onto a surface having a brush-like architecture formed of PEG 5000 and PEG 2000.

(Method and Result)

Figure 2:
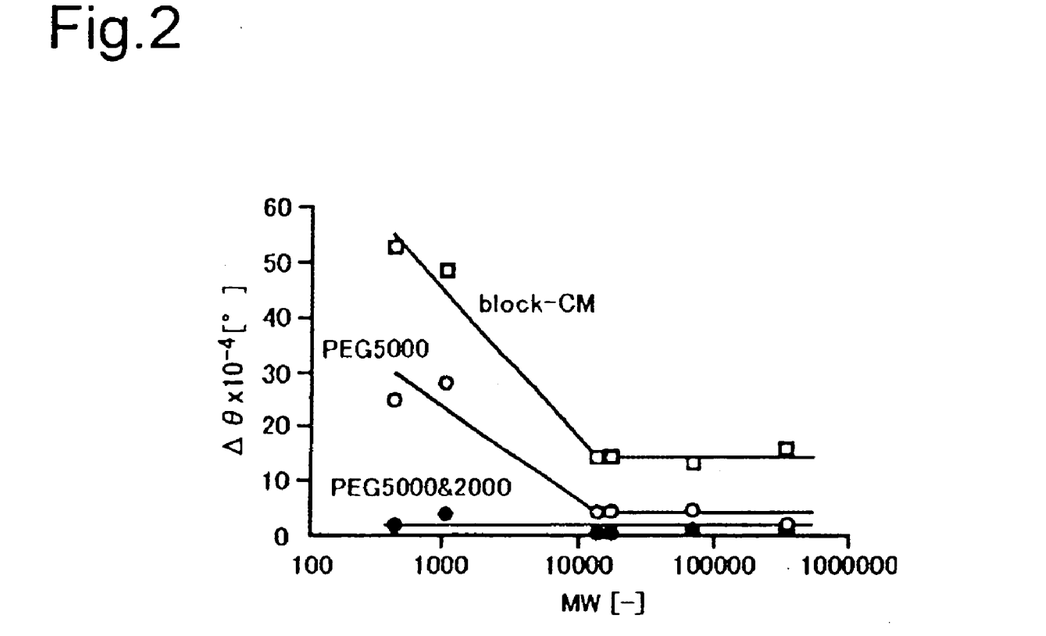
FIG. 2 is a graph showing adsorption behaviors of peptides and proteins of different molecular weights onto those surfaces.

A surface onto which acetal-PEG-SH (Mn=5000) was immobilized once, and the so formed surface onto which further acetal-PEG-SH (Mn=2000) having shorter molecular chain length was immobilized three times, were each purified. Over said surfaces a solution of 0.1 mg/ml of a peptide or protein in HEPES buffer [BIA-core; prepared by adding 3 mM EDTA and 0.005% (v/v) surfactant P20 to 0.15M-NaCl-containing 10 mM HEPES buffer (pH7.4)] was let flow each at a flow rate of 20 µl/min., reaction time, 10 minutes and at a temperature of 25° C. After injection of the solution onto each of the surfaces was completed, HEPES buffer was further let flow for 3 minutes, and then adsorption of the peptide or protein on each of the surfaces was quantified. The peptides and proteins selected for the test were as shown in Table 1 (fibrinogen, BSA, myoglobin, lysozyme, bradykinin and RGDS (single letter amino acid abbreviations). As controls, CM surface (commercial product of BIAcore) was used in the two forms of as marketed (normal-CM) and that on which the carboxyl terminals were blocked with ethanolamine (block-CM). The test results were as shown in FIG. 2.

TABLE 1

Characterization of Proteins and Peptides

| protein or peptide | MW [—] | pI [—] |
|---|---|---|
| fibrinogen | 340,000 | 6.0 |
| BSA | 68,000 | 4.8 |
| myoglobin | 17,600 | 6.8 |
| lysozyme | 14,300 | 10.9 |
| bradykinin | 1,060 | 12.5 |
| RGDS | 433 | 6.7 |

Figure 3:
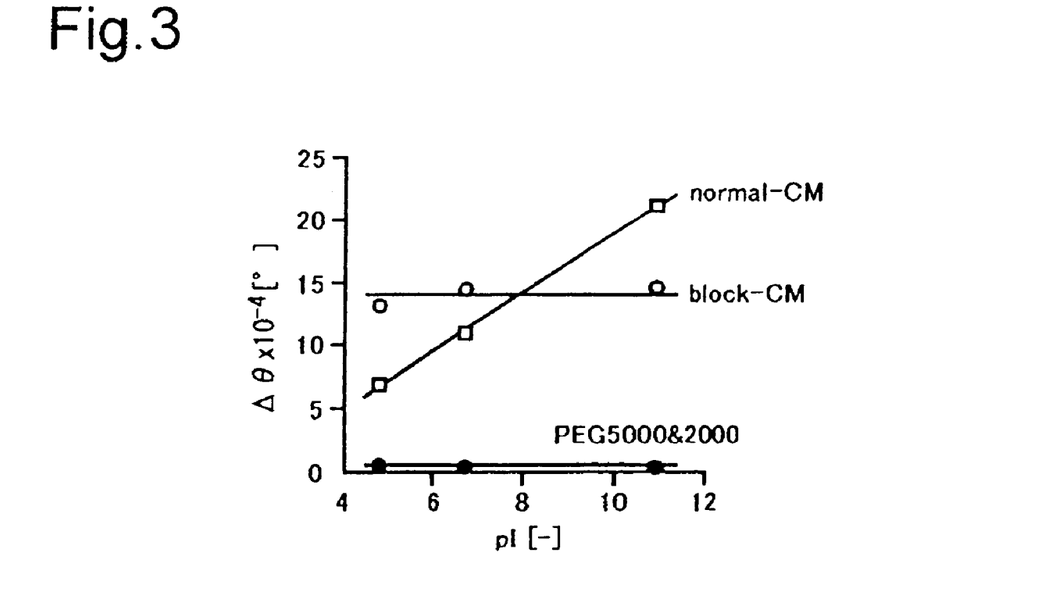
FIG. 3 is a graph showing adsorption behaviors of proteins having different proteinous isoelectric points onto those surfaces.

Non-specific adsorption of biomolecules of high molecular weight such as BSA onto the surface on which acetal-PEG-SH (Mn=5000) was immobilized once was suppressed, but non-specific adsorption of peptides (those having low molecular weight) such as RGDS was more than that of the BSA. This is presumably because the peptides had higher probability to intrude into the spaces between the PEG brush due to their low molecular weights, to increase the non-specific adsorption. Whereas, on the surfaces with increased PEG density made by further introducing to the surfaces PEG having a molecular weight of 2000, non-specific adsorption of peptides was drastically decreased. This is deemed to be the result of filling the spaces between the PEG brush with PEG of short chain length and whereby suppressing non-specific adsorption of low molecular weight substances. Furthermore the surfaces with PEG brush suppressed non-specific adsorption of peptides and proteins more than the blocked CM surfaces. The relevancy between isotonic point of protein and non-specific adsorption thereof is illustrated in FIG. 3. Because the normal-CM surface had carboxyl groups, non-specifically adsorbed quantity of the protein thereon changed as influenced by the isotonic point, while the isotonic point had no influence on the non-specific adsorption on the PEG brush surface and block-CM surface. From the foregoing, it can be said that suppression of non-specific adsorption of biomolecules such as protein on PEG brush surface largely depends on density of the PEG brush, while other factors such as the molecular weight (size), shape, electric charge and the like may also participate.

Evaluation of Influence on Molecule-recognizing Ability at Mixed Brush Surfaces (Influence on Sensor Sensitivity)

This test was conducted for obtaining the molecule-recognizing ability data at mixed brush surfaces, where ligand substances were bound to long chains or to short chains.

(Method and Result)

Preparation of Each Surface:
  (a) Plural surfaces onto which approximately same amount each of biotinylated PEG having a molecular weight of 2000 was introduced were prepared, and into a part of which acetal-PEG 5000-SH was introduced to form mixed brush surfaces (biotin-PEG 2000 surfaces and biotin-PEG 2000+PEG 5000 surfaces).
  (b) Plural surfaces onto which approximately same amount each of biotinylated PEG having a molecular weight of 2000 was introduced were prepared, and into a part of which acetal-PEG 2000-SH was further introduced to form surfaces with elevated brush density (biotin-PEG 2000 surfaces and biotin-PEG 2000+PEG 2000 surfaces).
  (c) Plural surfaces onto which approximately same amount each of biotinylated PEG having a molecular weight of 5000 was introduced were prepared, and into a part of which acetal-PEG 2000-SH was introduced to form mixed brush surfaces (biotin-PEG 5000 surfaces and biotin-PEG 5000+PEG 2000 surfaces).

Figure 4:
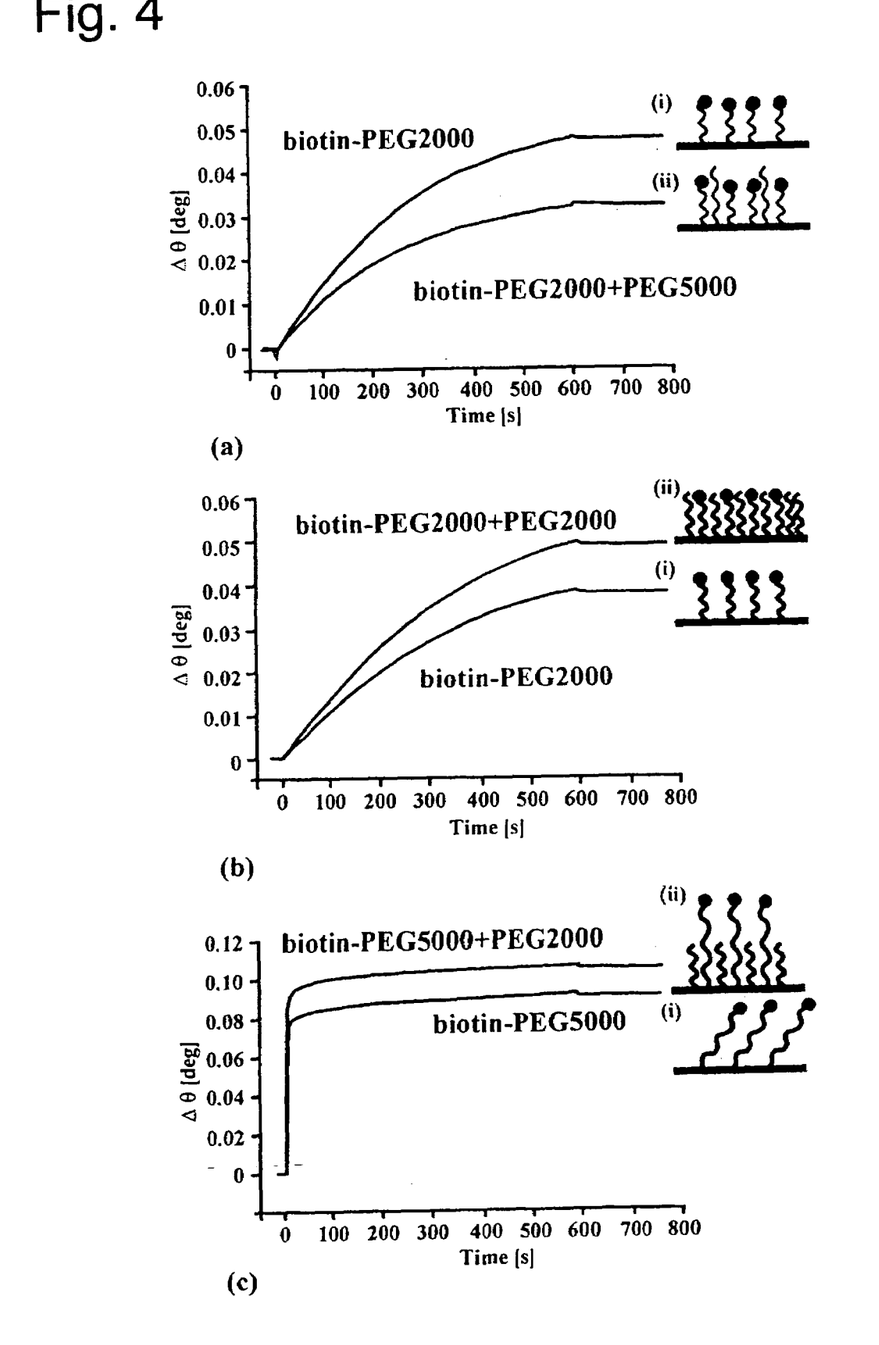
FIG. 4 are graphs showing the difference in interaction of ligand and analyte on those surfaces.

Molecule-recognizing Ability:

Then streptavidin solutions of identical concentration (0.1 mg/ml) were let flow over the above PEG brush surfaces, and the streptavidin bound to each of the surfaces was quantified. In consequence, it was found that (a) introduction of acetal-PEG 5000 decreased the quantity of streptavidin bound to the PEG brush surfaces [see FIG. 4($a$), ($b$) and ($c$)]. This suggests introduction of PEG molecules of long chain lengths onto the surfaces functions to interfere with ligand-analyte interaction. That is, the surface construction affects the surface's recognition ability of analyte. Whereas, (b) the surfaces whose PEG brush density was elevated by introduction of acetal-PEG 2000 having the same chain length showed increased quantity of streptavidin binding. As the reason for this increase, presumably the elevated density of the PEG chains facilitated vertical extension of the high molecular chains to increase bindability (molecule-recognizing ability) with the analyte. FIG. 4($c$) shows, similarly to (b), the introduction of said short chain length acetal-PEG 2000 to elevate the PEG chain density increased the quantity of streptavidin binding.

Where quantitative non-specific adsorption of BSA was compared as to (b), $\Delta\theta=24.3\times10^{-4}$ (the biotin-PEG 2000 surface) and $\Delta\theta=15.2\times10^{-4}$ (the acetal-PEG 2000+biotin-PEG 2000-composite surface) [°]. Thus, the mixed brush surface showed less BSA adsorption. This suppression of the non-specific adsorption also supports the presumed elevation in the PEG density. Based on the foregoing results, it is found that the architecture constructed on such PEG surfaces can control the ligand-analyte interaction.

Evaluation of Prior Art Surfaces with Respect to Non-specific Adsorption-suppressing Ability (Comparison)

As the prior art, aforesaid Roberts et al. and Holmlin et al. were given a reproducing test as follows.

For the purpose of evaluating quantitative non-specific adsorption on SAM-EO-utilizing surface; a surface formed by immobilizing EO chains of 9 EO segments on SAM was prepared.

(Method and Result)

The ability to suppress non-specific adsorption of protein on a surface utilizing self-assembling mono-molecular layer (SAM) was investigated (reproduction test of Roberts et al.) Onto a golden surface, 10-carboxy-1-decanethiol was immobilized, and on which $NH_2$-$EO_n$(n=9)-OH was bound. Over this surface a 1 mg/ml BSA solution was let flow and the non-specific adsorption of the protein was quantified. The resulting SPR angular change was $15.8\times10^{-4}$ deg., exhibiting a non-specific adsorption suppressing ability of the level same to that of the block-CM surface ($22.6\times10^{-4}$ deg.) and PEG 2000 (1) surface ($19.6\times10^{-4}$ deg.). However, the PEG 5000+2000-composite surface (no more than $5\times10^{-4}$ deg.) more significantly suppressed non-specific adsorption of BSA.

Method of Converting Functional Groups at PEG Chain Terminals

In the products of the foregoing Polymer Production Examples 1 and 2, e.g., acetal-PEG-SH, the acetal (or acetalized formyl groups) can be readily converted to aldehyde (or formyl), amino, or further to carboxyl groups, for example, by the following sequential procedures, retaining the state of being immobilized on the support surface:

(1) A gold substrate on which acetal-PEG-SH was immobilized was placed in a Schale, and immersed in 0.1 N HCL (pH2) solution under 3 hours' mild shaking. After completion of the reaction, the substrate was washed with distilled water.

(2) The substrate was placed in a Schale and immersed in 200 mM ammonium acetate solution [solvent: 150 mM NaCl-containing 50 mM PBS (pH 7.4)] under an hour's mild shaking. Thereafter 200 mM dimethylamineborane solution [solvent: 150 mM NaCl-containing 50 mM PBS (pH 7.4)] was added in three portions at 30 minutes' intervals.

After completion of the reaction the substrate was washed with 150 mM NaCl-containing 50 mM PBS (pH 7.4).

(3) Equimolar amounts of 0.7M succinic anhydride solution (solvent: THF) and triethylamine were mixed, and the substrate in a Schale was immersed in this mixture solution under an overnight's (O/N) mild shaking.

After completion of the reaction, the product was washed with THF and then with 150 mM NaCl-containing 50 mM PBS (pH 7.4).

Evaluation Test of the Influence of PEG Chain Terminal Groups on Non-specific Adsorption-suppressing Ability Non-specifically adsorbed protein was quantified on the surfaces on which the PEG chain terminal functional groups had been changed by the above-described conversion methods. In the earlier described test, solutions of each single protein were used, but for more practical use, bovine serum (mixed protein solution) was used in this test. Furthermore, data of PEGylated gold chip surfaces other than those manufactured by BIAcore [the data using Nippon Laser Co.'s apparatus (SPR-MACS)] are given herein, with the view to demonstrate that the same non-specific adsorption-suppressing ability of PEGylated chips was exhibited by those surfaces not manufactured by BIAcore as well.

(Method and Result)

Preparation of Mixed Brush Surfaces (While Flowing Immobilization was Adopted for BIACORE®, a Dipping System was Used in this Test.)

A 1 mg/ml acetal-PEG-SH (Mn=5000) solution in 1M-NaCl-containing 50 mM PBS (pH 7.4) was dropwisely applied to a gold substrate, followed by 30 minutes' standing at room temperature. Then the substrate was washed with 1M NaCl-containing 50 mM PBS (pH 7.4), dropwisely applied with 50 mM NaOH solution, allowed to stand for 30 seconds, and washed three times with 1M NaCl-containing 50 mM PBS (pH 7.4). The whole cycle of above treatments was repeated once again. Thereafter 1 mg/ml McO-PEG-SH (methoxy-terminated PEG instead of acetal terminals; having no reactivity) (Mn=2000) solution in 1 M NaCl-containing 50 mM PBS (pH 7.4) was dropwisely applied onto the substrate on which PEG 5000 was immobilized twice, followed by 30 minutes' standing at room temperature. Then the substrate was washed with 1 M NaCl-containing 50 mM PBS (pH 7.4). Onto the so washed surface 50 mM NaOH was dropwisely applied, allowed to stand for 30 seconds, and washed with 1 M NaCl-containing 50 mM PBS (pH 7.4) three times. The whole cycle of the above procedures was repeated twice. Thus a PEG 5000 (2)+PEG 2000 (3)-modified substrate was prepared.

Figure 5:
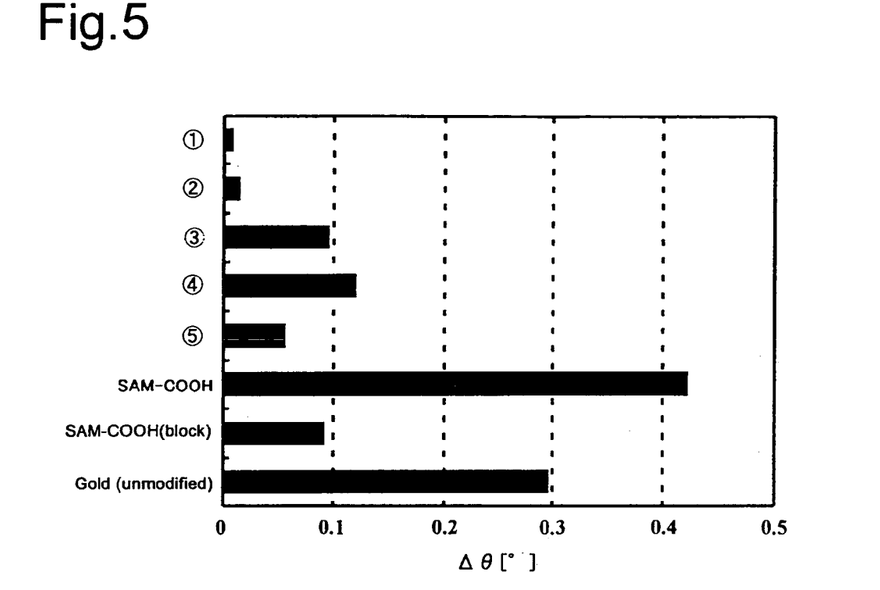
FIG. 5 is a graph showing adsorption behavior of protein onto the surfaces with various functional groups.

Evaluation Test of Non-specific Adsorption of Protein on Mixed PEG Brush Surfaces with Converted Terminal Functional Groups Over the following surfaces, a 15 mg/ml of fetal bovine serum (FBS) solution at 25° C. [solvent: 0.15 M-NaCl-containing 50 mM PBS (pH 7.4)] was let flow at a flow rate of 15 μl/min. for 4 minutes, three times. Thereafter a buffer solution [0.15 M-NaCl-containing 50 mM PBS (pH 7.4)] was let flow for 5 minutes, and the protein adsorption on each of the surfaces was quantified. The result was as shown in FIG. 5.

(Used Surfaces)
① Acetal-PEG surface
② CHO-PEG surface
③ $NH_2$-PEG surface
④ COOH-PEG-surface
⑤ COOH-PEG-surface (blocking)
⑥ SAM (4,4'-dithodibutyric acid) surface (COOH-terminal surface)
⑦ SAM (4,4'-dithiodibutyric acid) surface (COOH-terminal surface) (blocking)
⑧ Gold surface (unmodified surface)

Surfaces ①–④: See the earlier described conversion methods.

Surface ⑤: 1-Ethyl-3-(3-dimethylaminopropyl)carbodiimide (EDC) 25 mg was dissolved in 1 ml of distilled water. N-hydroxysuccinimide (NHS) 15 mg was dissolved in 9 ml of dioxane, and the two solutions were mixed. The substrate was immersed in this mixed solution under mild shaking at room temperature for 30 minutes for activation. Then the substrate was set on SPR apparatus, and onto which 1 M ethanolamine (pH 8.6) was injected at 25° C. at a flow rate of 5 μl/min. for 12 minutes, twice, to effect the blocking.

Surface ⑥: The gold substrate was placed in a Schale and immersed in 1 mM 4,4'-dithiodibutyric acid solution (solvent: ethanol) under mild shaking for 30 minutes. After completion of the reaction, the substrate was washed twice with ethanol.

Surface ⑦: See the surfaces ⑤ and ⑥.

Detection test of Low Molecular Weight Substance (Biotin: Mw=244)

Using the surfaces ④ (COOH-PEG-surface) and ⑥ [SAM (4,4'-dithiodibutyric acid) surface (COOH terminal surface) as used in the FBS adsorption evaluation test, streptavidin was immobilized on those surfaces and D-biotin detection was conducted.

(Method and Result)

EDC 25 mg was dissolved in 1 ml of distilled water, and mixed with a solution of 15 mg of NHS as dissolved in 9 ml of dioxane. In this mixed solution the substrates [said surfaces ④ (COOH-PEG-surface) and ⑥ (SAM (4,4'-dithiodibutyric acid) surface (COOH terminal surface)] were immersed under mild shaking at room temperature for 30 minutes for activation. Then the substrates were set on SPR apparatus and onto which 0.1 mg/ml streptavidin solution [solvent: 150 mM NaCl-containing 50 mM PBS (pH 7.4)] was injected under the conditions of 25° C. and 5 μl/min. for 12 minutes, twice. Thereafter 1 M ethanolamine (pH 8.6) was injected once (12 minutes) to block unreacted activated ester.

Onto these streptavidin-immobilized surfaces 1 mg/ml D-biotin solution [solvent: 150 mM NaCl-containing 50 mM PBS (pH 7.4)] was injected twice (12 minutes×2 times), followed by a buffer infection for 5 minutes. Then the biotin linked to the surfaces was quantified, with the result as shown in FIG. 6.

Figure 6:
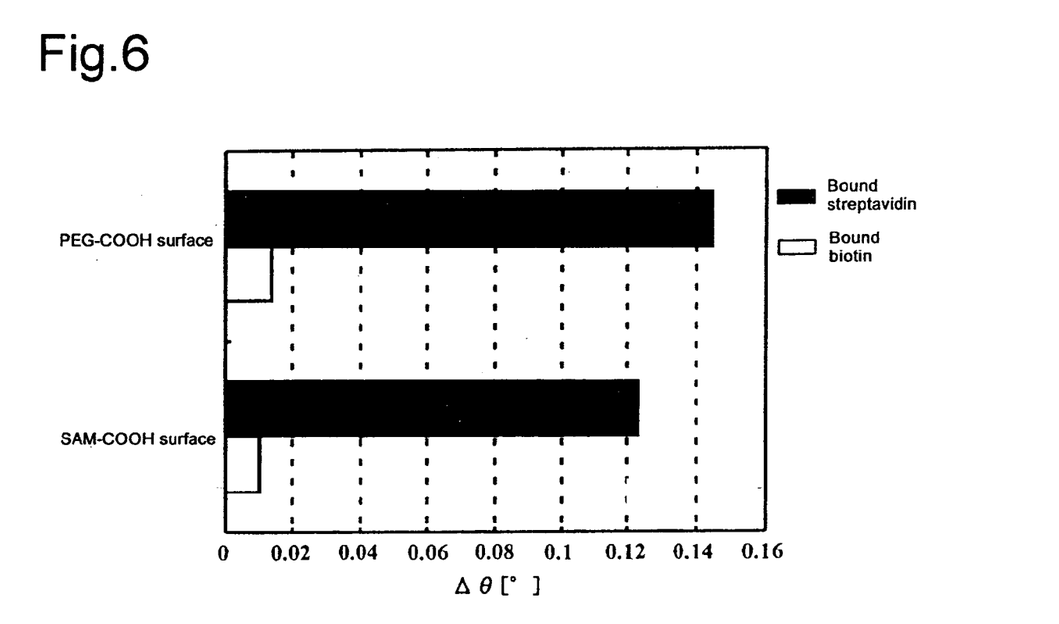
FIG. 6 is a graph showing adsorption behavior of biotin onto a PEG surface and SAM (carrying low molecular weight EO) surface.

From FIG. 6 it is found that both of the surfaces enable detection of low molecular weight biotin. However, the ability to suppress surfacial non-specific adsorption of biotin of PEG brush surfaces is higher.

Evaluation Test of Molecule-recognizing Ability in Mixed Protein Solution, by Means of Streptavidin Detection in the Concurrent Presence of BSA (Method and Result)

Streptavidin-recognizing ability of a composite surface constructed of acetal-PEG-SH (Mn=5000 and 2000) was investigated, in which PG 5000 and 2000 (2) (2:2) surface formed by simultaneously introducing PEG 5000 and PEG 2000 onto a gold surface was used.

After immobilizing the PEG's on said surface, 0.01N HCl solution was let flow over the surface to convert the acetal groups to aldehyde groups. Then a biotin hydrazide solution [solvent: 50 mM PBS (pH 7.4)] was let flow over the same surface to cause biotin-binding.

Figure 7:
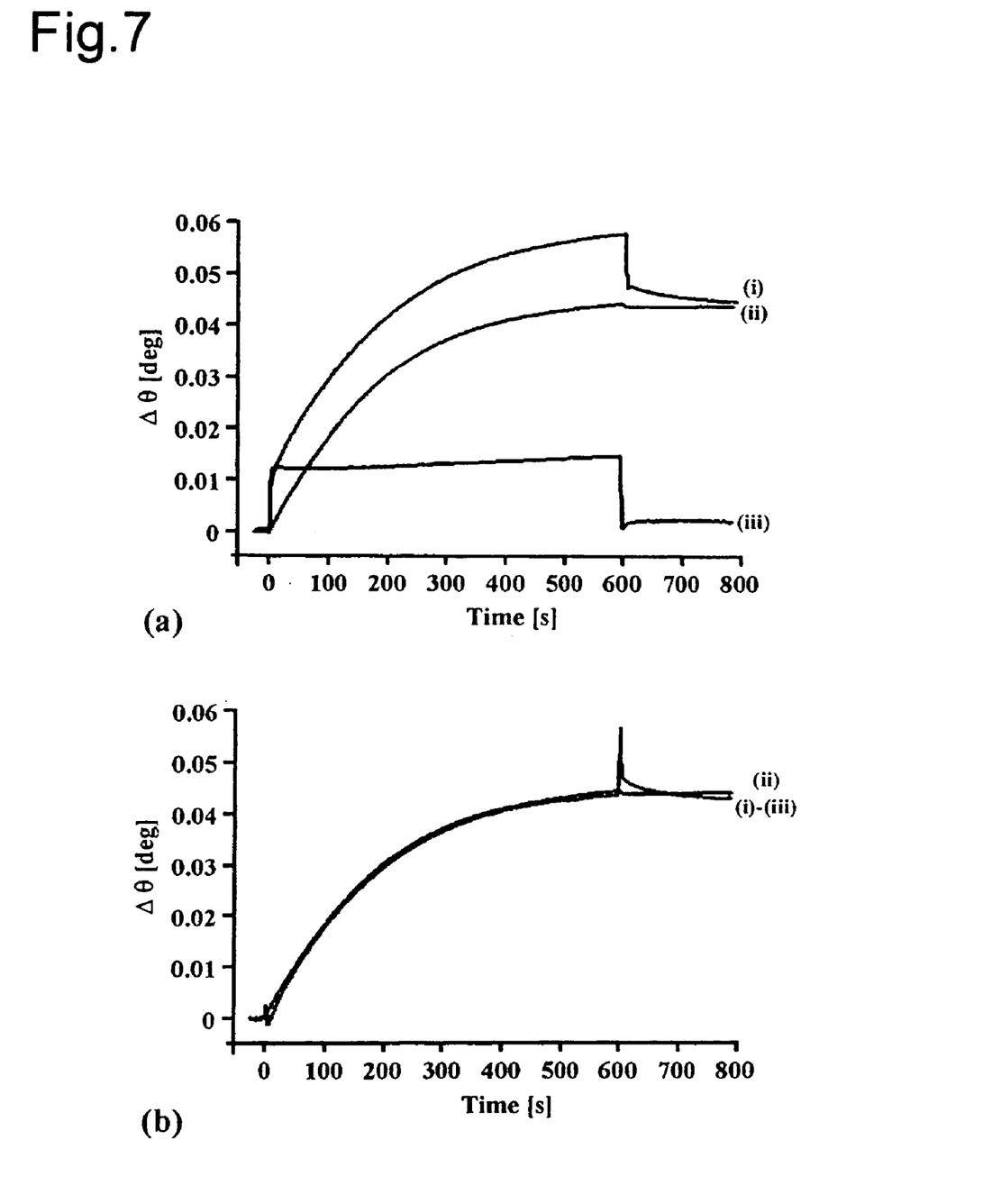
FIG. 7 is a graph showing the influence of BSA present as an impurity protein on detection of streptavidin.

Over said biotin-PEG surface, (i) 1 g/L-BSA+0.1 mg/L-streptavidin solution, (ii) 0.1 mg/L-streptavidin solution or (iii) 1 g/L-BSA solution was let flow and their binding to respective surfaces was quantified. In consequence, it was found that the biotin-PEG immobilized surface recognized streptavidin alone, in spite of the difference in concentration between BSA and streptavidin that the former was 10,000 times that of the latter, indicating its high molecule-recognizing ability [cf. FIG. 7(a)]. Furthermore, when the numerical values (i) on the 7(a) graph as obtained in the occasion of flowing the BSA/streptavidin mixed solution minus those (iii) of flowing the BSA alone, i.e., (i)–(iii), were plotted, the graph approximately coincided with that of the case wherein the streptaviden solution alone was flowed [cf. FIG. 7(b)]. From this result also the PEG brush surfaces are verified to have high molecule-recognizing ability.

INDUSTRIAL APPLICABILITY

According to the present invention, sensor chip surfaces are provided onto which non-specific adsorption of living organism-derived proteins is markedly suppressed. Therefore, the present invention is utilizable in the trade of manufacturing bioassaying machinery and tools and of clinical diagnoses.

What is claimed is:

1. A method for preparing a biosensor chip comprising two groups of polymers expressed by the following general formula (I) which are linked onto the sensor chip surface via the A-moiety present at one end of said polymers:

general formula (I)

$$A\text{-}(CH_2)_p\text{-}L_1\text{-}(CH_2C_2O)_n\text{-}L_2\text{-}X \qquad (I)$$

in which
A stands for HS— group,
$L_1$ stands for a first linker or valence bond,
$L_2$ stands for a second linker or valence bond,
X stands for hydrogen, a functional group, protected functional group or ligand,
p is an integer of 2–12, and
n is an integer of, on the average, 10–10,000,
in which one group of said polymers have an integer, n, as an average value, of 50–10,000
and the other group of said polymers have an integer, n, as an average value less than that of said one group by at least 10, which comprises, (A) a step of contacting an aqueous solution of said one group of polymers expressed by a general formula (Ia):

$$HS\text{—}(CH_2)_p\text{-}L_1\text{-}(CH_2CH_2O)_n\text{-}L_2\text{-}X \qquad (Ia)$$

in which $L_1$, $L_2$, X, p and n have the same significations to those as defined as to the general formula (I),
with the sensor chip surface of a metal selected from the group consisting of gold, silver, copper and aluminum, under the conditions sufficient to link a prescribed amount of said polymer to said metallic surface, and thereafter washing away the unlinked polymer;

(B) a step of subsequently contacting an aqueous solution of said other group of polymers of general formula (Ia) which have an integer, n, as an average value, less than that of said one group of polymers in step (A) by at least 10, with the sensor chip surface which has undergone the above step A, under the conditions sufficient to link said polymer to said surface, and thereafter washing away the unlinked polymer; and (C) repeating the above step (A), (B) or both steps (A) and (B) plural times to obtain said biosensor chip.

2. A method for treating the surface of a material selected from the group consisting of glass, semi-conductor, ceramic, metal oxide and alloy oxide, where two groups of polymers expressed by the following general formula (I) are linked onto the surface via the A-moiety present at one end of said polymers:

$$A\text{-}(CH_2)_p\text{-}L_1\text{-}(CH_2CH_2O)_n\text{-}L_2\text{-}X \qquad \text{general formula (I)}$$

in which
A stands for group,
where $R^1$, $R^2$ and $R^3$ each independently stands for $C_1$–$C_6$ alkyl,
$L_1$ stands for a first linker or valence bond,
$L_2$ stands for a second linker or valence bond,
X stands for hydrogen, a functional group, protected functional group or ligand,
p is an integer of 2–12, and
n is an integer of on the average, 10–10,000,
in which one group of said polymers have an integer, n, as an average value, of 50–10,000
and the other group of said polymers have an integer, n, as an average value, less than that of said one group by at least 10, which comprises (A) a step of contacting an organic solvent solution of said one group of polymers expressed by a general formula (Ib):

in which $R^1$, $R^2$, $R^3$, $L_1$, $L_2$, X, p and n have the same significations to those as defined as to the general formula (I), with said material under the conditions sufficient to adhere or link a prescribed amount of said polymer to the surface of said material, distilling the solvent off, and washing away the unlinked polymer;

(B) a step of subsequently contacting an organic solvent solution of said other group of polymers of the general formula (Ib) which have an integer, n, as an average value, less than that of the polymer in step (A) by at least 10, with the surface which has undergone the above step (A) under the conditions sufficient to adhere or link said polymer to said surface, then distilling the solvent off and washing away the unlinked polymer; and (C) repeating the above step (A), (B) or both steps (A) and (B) plural times to obtain said sensor biochip.

* * * * *